(12) United States Patent
Lashkari et al.

(10) Patent No.: US 10,039,790 B2
(45) Date of Patent: Aug. 7, 2018

(54) ISOLATION AND THERAPEUTIC APPLICATION OF ADULT RETINAL STEM CELLS COLLECTED FROM EXTRA-RETINAL TISSUES

(71) Applicant: The Schepens Eye Research Institute, Inc., Boston, MA (US)

(72) Inventors: Kameran Lashkari, Boston, MA (US); Marie Shatos, Athol, MA (US); Tat Fong Ng, Somerville, MA (US)

(73) Assignee: The Schepens Eye Research Institute, Inc., Boston, MA (US)

(*) Notice: Subject to any disclaimer, the term of this patent is extended or adjusted under 35 U.S.C. 154(b) by 0 days.

(21) Appl. No.: 14/744,549

(22) Filed: Jun. 19, 2015

(65) Prior Publication Data

US 2016/0143954 A1    May 26, 2016

Related U.S. Application Data

(63) Continuation of application No. 12/299,357, filed as application No. PCT/US2007/003921 on Feb. 15, 2007, now Pat. No. 9,061,017, which is a continuation-in-part of application No. PCT/US2006/017861, filed on May 3, 2006.

(51) Int. Cl.
| | |
|---|---|
| *C12N 5/00* | (2006.01) |
| *C12N 5/02* | (2006.01) |
| *C12N 5/071* | (2010.01) |
| *A61K 35/30* | (2015.01) |
| *A61K 35/44* | (2015.01) |
| *C12N 5/079* | (2010.01) |
| *C12N 5/0797* | (2010.01) |
| *A61K 9/00* | (2006.01) |
| *A61K 45/06* | (2006.01) |

(52) U.S. Cl.
CPC ............ *A61K 35/30* (2013.01); *A61K 9/0048* (2013.01); *A61K 35/44* (2013.01); *A61K 45/06* (2013.01); *C12N 5/0621* (2013.01); *C12N 5/0623* (2013.01); *C12N 2501/11* (2013.01); *C12N 2501/115* (2013.01)

(58) Field of Classification Search
CPC ..... C12N 5/0621; C12N 5/0623; A61K 35/30
USPC ........................................ 435/325, 366, 375
See application file for complete search history.

(56) References Cited

U.S. PATENT DOCUMENTS

| | | | |
|---|---|---|---|
| 6,117,675 | A  | 9/2000  | van der Kooy et al. |
| 6,238,922 | B1 | 5/2001  | Uchida |
| 6,610,535 | B1 | 8/2003  | Lu et al. |
| 7,514,186 | B2 | 4/2009  | Meijer et al. |
| 2003/0148513 | A1 | 8/2003  | Sugaya et al. |
| 2003/0207450 | A1 | 11/2003 | Young et al. |

FOREIGN PATENT DOCUMENTS

| | | |
|---|---|---|
| WO | WO-2000/047238 A1 | 8/2000 |
| WO | WO-2004/007749 A2 | 1/2004 |
| WO | WO-2005054447 A2 | 6/2005 |

OTHER PUBLICATIONS

Kolf et al., 2007, Arthritis Research & Therapy, vol. 9, p. 204, 10 pages.*
Alenzi et al., 2011, African Journal of Biotechnology, vol. 10(86), pp. 19929-19940.*
Wu et al., 2012, Aging Research reviews, vol. 11, p. 32-40.*
Steinert et al., 2007, Arthritis Research & therapy, vol. 9, No. 3, 213, p. 1-15.*
Li et al., 2009, Transplant Immunology, vol. 21, p. 70-74.*
Sprangers et al., 2008, Kidney International, vol. 74, p. 14-21.*
Abeyta et al., "Unique gene expression signatures of independently-derived human embryonic stem cell lines." Human Molecular Genetics, 13(6): 601-608 (2004).
Allegrucci et al., Human Reproduction Update, vol. Advance Access published on Aug. 26, 2006, p. 1-18.
Coles, Elk., et al., "Facile isolation and the characterization of human retinal stem cells", Proceedings of the National Academy of Science, 101(44):15772-15777 (2004).
Cotsarelis, G., "Gene expression profiling gets to the root of human hair follicle stem cells." The Journal of Clinical Investigation, 116:(1)19-22. (2006).
Kohno, Investigative Ophthalmology & Visual Science. (ARVO); 45: Abstract 5382 (2004).

(Continued)

*Primary Examiner* — Shin Lin Chen
(74) *Attorney, Agent, or Firm* — Mintz Levin Cohn Ferris Glovsky and Popeo, P.C.; Ingrid A. Beattie

(57) ABSTRACT

The present invention is directed to an adult retinal cell line isolated from extra-retinal ocular tissue, and methods of isolating adult retinal cells from extra-retinal ocular tissue. The present invention is further directed to adult retinal stem cells isolated from vestigial tissue dissected from the eye of a donor mammal suffering from persistent fetal vasculature. The present invention is further directed to a culture medium for growing or maintaining retinal stem cells, and methods of maintaining adult retinal cells in culture. The present invention is further directed to methods of treating a treating an eye with retinal dystrophy using retinal stem cells, and an eye with glaucomatous injury with retinal stem cells. The present invention is further directed to kits for harvesting extra-retinal ocular tissue comprising a sterile container and a harvesting solution, wherein the kit allows the survival of the tissue until later dissociation of cells from the tissue.

6 Claims, 7 Drawing Sheets

(56) References Cited

OTHER PUBLICATIONS

Limb et al., Investigative Ophthalmology & Visual Science. 45 Abstract 5387 (2004).
Marcos et al., "Retinal stem cells in vertebrates: parallels and divergences." Int. J. Dev. Biol. 48:993-1001 (2004).
PCT International Search Report: PCT/US 2006/017861; Publication No. W02007/130060 "Isolation and therapeutic application of adult retinal stem cells collected from ex-tra-retinal tissues" dated Jul. 2, 2008.
PCT International Search Report: PCT/US 2007/003921; Publication No. W02007/130191 "Isolation and therapeutic application of adult retinal stem cells collected from ex-tra-retinal tissues" dated Feb. 4, 2008.
Rao, M., "Conserved and divergent paths that regulate self-renewal in mouse and human embryonic stem cells." Developmental Biology, 275:269-286 (2004).
Saint-Geniez et al., "Development and pathology of the hyaloid, choroidal and retinal vasculature." Int. J. Dev. Biol. 48:1045-1058 (2004).
Sato et al., "Molecular signature of human embryonic stem cells and its comparison with the mouse." Developmental Biology, 260:404-413 (2003).
Yu et al., "Fluorescence excitation and emission spectroscopy of the A1A <--X1A system of CHBr." American Journal of Pathology, 168(6):1-6. (2006).
Modrzejewska et al., "Persistent fetal vasculature syndrome—clinical image and diagnostic difficulties." 113: 357-363 (2011).

\* cited by examiner

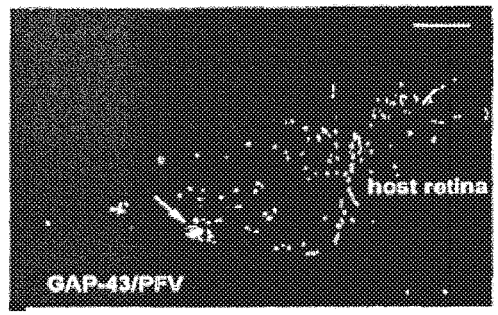 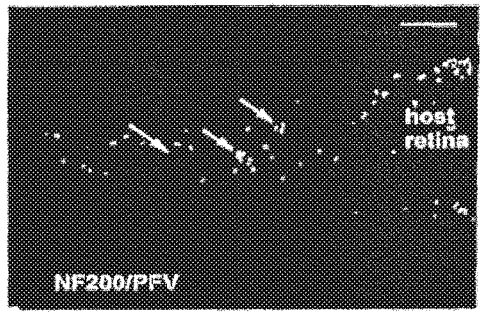
FIG. 7A  FIG. 7B
 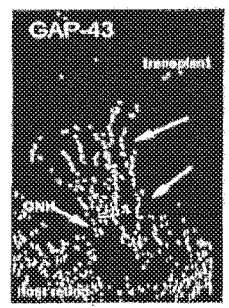
FIG. 7C  FIG. 7D
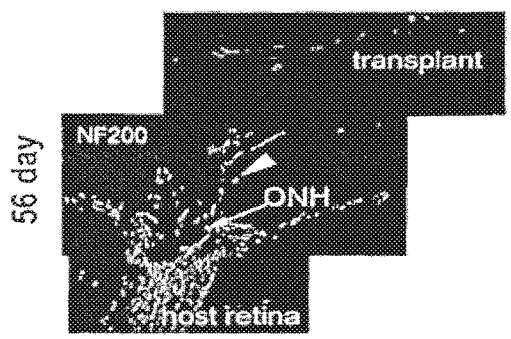 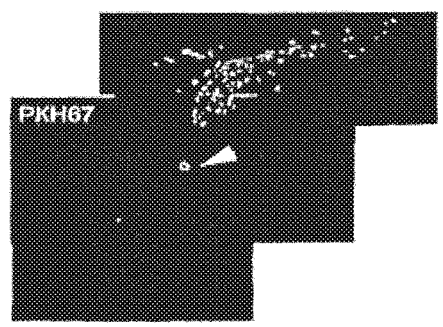
FIG. 7E  FIG. 7F

ISOLATION AND THERAPEUTIC APPLICATION OF ADULT RETINAL STEM CELLS COLLECTED FROM EXTRA-RETINAL TISSUES

CROSS REFERENCE TO RELATED APPLICATIONS

The present application is a continuation of U.S. application Ser. No. 12/299,357 filed Jan. 14, 2009 (now U.S. Pat. No. 9,061,017 issued Jun. 23, 2015), which is a 35 U.S.C. 371 National Stage Application of International Application No. PCT/US2007/003921, International Filing Date: Feb. 15, 2007, which is a continuation in part of International Application No. PCT/US2006/017861, International Filing Date: May 3, 2006, each of which are incorporated herein by reference in its entirety.

FIELD OF THE INVENTION

The present invention is directed to an adult retinal stem cell line isolated from extra-retinal ocular tissue, and methods of isolating adult retinal stem cells from extra-retinal ocular tissue. The present invention is further directed to adult retinal stem cells isolated from vestigial tissue dissected from the eye of a donor mammal suffering from persistent fetal vasculature. The present invention is further directed to a culture medium for growing or maintaining retinal stem cells, and methods of maintaining adult retinal cells in culture. The present invention is further directed to methods of treating an eye with retinal dystrophy using retinal stem cells, and an eye with glaucomatous injury with retinal stem cells. The present invention is further directed to kits for harvesting extra-retinal ocular tissue comprising a sterile container and a harvesting solution, wherein the kit allows the survival of the tissue until later dissociation of cells from the tissue.

BACKGROUND OF THE INVENTION

Among heritable conditions alone, there are over 100 examples of diseases involving the loss of retinal neurons. For example, glaucoma is one of the leading causes of blindness in the world. Approximately, 2.5 million people in the United States have glaucoma and more than 130,000 people are legally blind from the disease. Glaucoma presents a complex pathology. It is characterized by retinal and optic nerve neuropathies, eventually leading to death of retinal ganglion cells (RGCs) and their axons, as well as the excavation of the optic nerve head. In addition, chronic open angle glaucoma is often associated with elevated intraocular pressure (IOP) resulting from increased resistance to drainage of the aqueous humor. Many types of glaucoma have been described including pigment dispersion syndrome and pseudoexfoliation of the lens which is characterized by the deposition of pigment granules and an aberrant protein, respectively, throughout the anterior segment of the eye.

One potential strategy for treating glaucoma and other types of disorders is to transplant retinal stem cells into the eye of the diseased donor. After transplantation, these retinal stem cells could then differentiate, allowing repair of the diseased eye. Because of the ethical and governmental restrictions on the use of embryonic stem cells, there is a real interest in developing materials and methods involving adult retinal stem cells rather than embryonic retinal stem cells. However, the success of adult retinal stem cell transplantation is dependent on a number of factors.

For example, clinical outcomes for patients undergoing transplantation have traditionally been affected by adverse immune responses provoked by the transplanted cells. Use of autologous cells can minimize or eliminate such adverse reactions. Previously, retinal stem cells have been isolated directly from the retina or retinal pigment epithelium. Performance of this isolation procedure, however, results in partial traumatic injury to these tissues or complete destruction of the retina or retinal pigment epithelium. Hence, using these techniques, it is impossible to harvest retinal stem cells from the intended recipient without partial or complete injury to the eye of the recipient/donor. Accordingly, there is a need to develop methods of isolating retinal stem cells without injury or destruction of the retina or retinal epithelium, thereby allowing the transplantation of autologous retinal stem cells.

Additionally, successful use of adult retinal stem cells lines for transplantation has been impeded by the difficulty in propagating and maintaining adult cell lines. Unlike embryonic stem cells, adult stem cells have a self-limited life span. Therefore, adult stem cells must be used immediately after culturing, making it necessary to have a donor on hand for any successful transplantation procedure. Hence, there is a need to develop methods of growing and maintaining adult retinal stem cells in culture, thereby increasing the bank of donor cells available for transplantation. This invention fulfills these needs and others.

SUMMARY OF THE INVENTION

The present invention provides methods of isolating retinal stem cells from extra-retinal ocular tissue comprising dissociating the retinal stem cells from the extra-retinal ocular tissue.

The present invention further provides an adult retinal stem cell line isolated from extra-retinal ocular tissue.

The present invention further provides culture media for growing or maintaining adult retinal stem cells comprising:
  a serum-free culture medium;
  a first growth factor comprising from about 0.1 ng/mL to about 40 ng/mL of the serum-free culture medium;
  a second growth factor comprising from about 0.1 ng/mL to about 40 ng/mL of the serum-free culture medium;
  a first neural supplement for enhancing neuronal progenitor cell growth comprising from about 0.1% v/v to about 10% v/v of the total culture medium;
  optionally, a second neural supplement for enhancing neuronal progenitor cell growth comprising from about 0.1% v/v to about 10% v/v of the total culture medium; and
  optionally, a high-grade of heat-inactivated serum comprising from about 0.1% v/v to about 20% v/v of the total culture medium;
  provided that the culture medium does not comprise neuroprogenitor cell-conditioned medium.

The present invention further provides methods for maintaining adult retinal stem cells in culture comprising culturing the retinal stem cells in the culture media of the invention.

The present invention further provides methods of treating a dystrophic eye, comprising introducing autologous retinal stem cells into an eye of a mammalian recipient.

The present invention further provides use of autologous retinal stem cells in a method of treating a dystrophic eye of a mammal.

The present invention further provides adult retinal stem cells isolated from vestigial tissue dissected from the eye of a donor mammal suffering from persistent fetal vasculature.

The present invention further provides methods of treating a dystrophic eye of a mammal, by introducing the adult retinal stem cells isolated from vestigial tissue dissected from the eye of a donor mammal suffering from persistent fetal vasculature into the eye of the mammal.

The present invention further provides a method of replenishing retinal ganglion cells comprising introducing the adult retinal stem cells into the eye of the mammal, wherein the adult retinal stem cells are isolated from vestigial tissue dissected from the eye of a donor mammal suffering from persistent fetal vasculature.

The present invention further provides a method of replenishing retinal ganglion cells comprising introducing autologous adult retinal stem cells into the eye of the mammal.

The present invention further provides use of adult stem cells isolated from vestigial tissue dissected from the eye of a donor mammal suffering from persistent fetal vasculature in a method of treating a dystrophic eye of a mammal.

The present invention further provides a kit for harvesting extra-retinal ocular tissue comprising a sterile container and a harvesting solution, wherein the kit allows the survival of the tissue until later dissociation of cells from the tissue.

BRIEF DESCRIPTION OF THE FIGURES

FIGS. 7(a) and 7(b) depict the transplantation of cells into the vitreous of the C57BL/6 mice 25 after 3 days, showing the expression of GAP-43 (FIG. 7a, arrow) in the cell bodies and the expression of NF-200 in the neurites (FIG. 7b, arrows). The original transplanted PFV cells are tagged with a fluorescent rhodamine marker (red).

FIG. 7(c) depicts the transplantation of cells into the vitreous of the C57BL/6 mice after 28 days, showing the formation of an aggregate linked to the optic nerve head (ONH) by a stalk-like structure, as well as the expression of NF-200 in the stalk-like structure.

FIG. 7(d) depicts the transplantation of cells into the vitreous of the C57BL/6 mice after 28 days, showing the formation of an aggregate linked to the optic nerve head (ONH) by a stalk-like structure, as well as the expression of GAP-43 in the stalk-like structure (arrows). FIG. 7(d) also depicts the extension of GAP-43 expressing fibers into the optic nerve head.

FIG. 7(e) depicts the transplantation of cells into the vitreous of the C57BL/6 mice after 56 days, showing expression of NF-200 in the stalk-like structure that extends into the optic nerve head (arrow). A bridge is formed between the transplanted cells and the recipient (arrowhead).

FIG. 7(f) depicts the same specimen as in FIG. 7(e) showing red fluorescence of rhodamine-labeled cells into the vitreous of the C57BL/6 mice after 56 days. A bridge is visualized between the transplanted cells and the recipient (arrowhead).

DETAILED DESCRIPTION OF THE INVENTION

Figure 1:
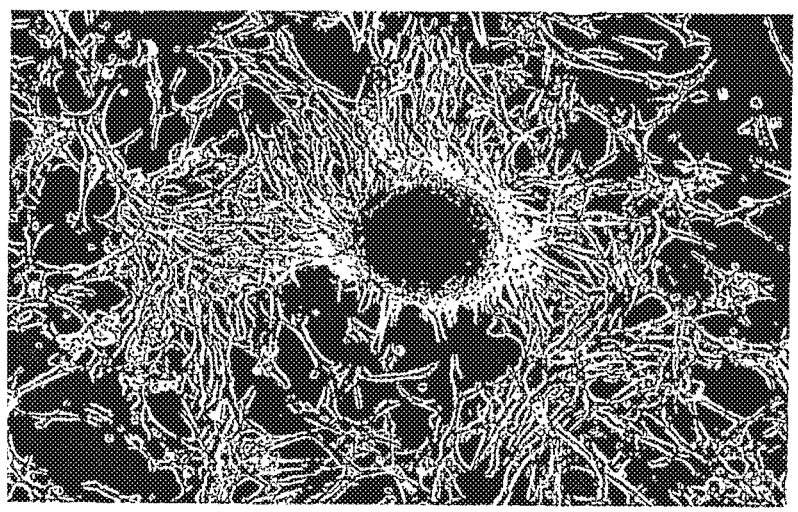
FIG. 1 depicts the formation of neurospheres by stem cells isolated from human persistent fetal vasculature (PFV) membrane and grown under tissue culture conditions.

In one aspect, the present invention provides a method of isolating adult retinal stem cells from non-retinal sources in which the host retinal tissue is not traumatized or destroyed. While retinal stem cells can be isolated from the retina or retinal epithelium, the isolation procedure results in partial traumatic injury or complete destruction of the retina or retinal epithelium tissues of the donor.

Advantageously, the present invention relates to the discovery that retinal stem cells can be isolated from adult extra-retinal tissue, thereby eliminating injury to retina or retinal epithelium tissues. Accordingly, the present invention provides a method of isolating retinal stem cells from extra-retinal ocular tissue comprising dissociating the retinal stem cells from the extra-retinal ocular tissue. Because there is no destruction of donor's retinal tissues, the method of the invention allows the isolation of retinal stem cells from a donor for autologous cell transplant, or alternatively, for transplant into the eye of another subject. Autologous retinal stem cell transplants cannot be achieved with prior methods.

The non-retinal tissue useful for the methods of the invention can be dissected from the underlying retina during conventional vitreo-retinal surgery. These tissues were historically considered to be disorganized scar tissue and, therefore, were typically discarded after surgery. Surprisingly, it has been discovered that these tissues have a complicated cellular composition and do in fact contain retinal stem cells. These tissues can be collected and subjected to isolation techniques described herein. Stem cells can be extracted, propagated-in culture and used for transplantation. Because it uses normally discarded extra-retinal tissues, the method of the present invention provides an additional advantage in eliminating wasteful disposal.

The extra-retinal tissues useful in the present invention include, but are not limited to, extra-retinal tissues of eyes with various congenital and neovascular conditions. These include (1) disorganized retrolental tissues from eyes with persistent hyperplastic primary vitreous (PHPV), also known as persistent fetal vasculature (PFV). This condition is herein referred to as PFV. (2) retrolental and neovascular tissue from eyes with advanced (stages 4 and 5) retinopathy of prematurity (ROP); and (3) pupillary membranes originating from ciliary processes and other extra-retinal tissue of eyes with ischemic or non-ischemic retinopathy.

Accordingly, in some embodiments of the method of the invention, the extra-retinal ocular tissue is a vestigial tissue dissected from the eye of a donor mammal suffering from PFV, a neovascular membrane dissected from the eye of a donor mammal suffering from ROP, or a pupillary membrane dissected from the eye of the donor mammal suffering from an inflammatory condition.

As used herein, the term "extra-retinal ocular tissue" refers to tissue from the eye that is not retinal tissue or retinal epithelium tissue.

In some embodiments of the invention, the extra-retinal ocular tissue is a vestigial tissue dissected from the eye of a donor mammal suffering from PFV, a condition in which the hyaloidal vessels that normally feed the developing lens of the eye during embryonic development do not normally regress. This vestigial tissue grows autonomously as a membrane resembling a scar tissue within the retrolental space and pushes the lens forward into the anterior chamber of the eye, causing angle closure glaucoma. Additionally, the retina may be dragged into the membrane resulting in a type of tractional retinal detachment. During surgical repair of these eyes, this membrane is carefully dissected from the underlying retina and the neighboring ocular structures such as the ciliary body, and can be removed en bloc.

Characterization of the cellular composition of these membranes has shown them to be comprised of networks of endothelial (vascular) and neuronal/glial structures. This network also contains nestin positive cells that represent neuronal progenitor or stem cells. While not wishing to be bound by any particular theory, it is believed that there is a stem cell niche within these membranes composed of small populations of adult neuronal cells surrounded by feeding capillaries (endothelial cells) with nestin positive cells at the center. These stem cells have been extracted from these membranes and used to develop a cell line in tissue culture. This cell line is self propagating and has all characteristics of neuronal stem cells. For example, these stem cells express the neurofilament nestin and can develop neurospheres in culture. Under specific culture conditions these cells differentiate into mature cells and express markers consistent with mature neurons and retinal elements. These cells have also been integrated into chick retina, where they were found to differentiate into cells expressing an endothelial marker and induced the host retina to sprout axonal elements that penetrate them. These cells have been found not to express photoreceptor markers in culture, unlike stem cells isolated from the tissues of the retina or retinal epithelium. For example, these cells were found not to express rhodopsin and recoverin, two photoreceptor markers, in culture. This surprising lack of photoreceptor marker expression indicates that retinal stem cells isolated from PFV tissue are much different than those isolated from retinal and retinal epithelium tissue.

In some embodiments of the method of the invention, the extra-retinal ocular tissue is a neovascular membrane dissected from the eye of a donor mammal suffering from retinopathy of prematurity. Retinopathy of prematurity (ROP) is a leading cause of neonatal blindness in premature infants, heralded by low birth weight and oxygen supplementation. In the setting of ROP, retinal vascularization is interrupted by premature birth and placement of the newborn in a high oxygen environment. After the newborn is returned to ambient oxygen, the vascularization resumes in a robust manner, inducing growth of neovascular tissue at the border between the vascularized and avascular retina. In advanced cases of this condition, a robust neovascular membrane grows over the retina causing partial (stage 4) or complete (stage 5) traction retinal detachment. As a result, the retina of these eyes degenerates into a condition that mimics eyes with retinitis pigmentosa and patients are left blind. As part of the treatment of advanced ROP, the neovascular membrane is carefully dissected from the underlying detached retina and can be removed en bloc. An analysis of these membranes shows that they also harbor nestin expressing stem cells, which can be differentiated into mature neuronal and retinal elements.

In some embodiments, the extra-retinal ocular tissue is a pupillary membrane dissected from the eye of the donor mammal suffering from an inflammatory condition. In some embodiments, the pupillary membranes rise from inflammatory conditions that include diabetic retinopathy, advanced retinal detachment, and chronic inflammation. In some embodiments, the chronic inflammation is a result of multiple ocular surgeries or trauma.

These pupillary membranes arise from the ciliary sulcus and ciliary body area, cover the retrolental space and occlude the pupil. These membranes also harbor nestin-expressing stem cells which can be differentiated into mature neuronal and retinal elements. The cells isolated from these pupillary membranes have expressed nestin in culture.

The characterization of the retinal stem cells obtained from these membranes can be accomplished by immunocytochemistry (ICC) and reverse-transcriptase polymerase chain reaction (RT-PCR) by techniques known to one of skill in the art. Primary and secondary antibodies suitable for use in detecting various cell markers by ICC are summarized in Tables 1 and 2. RT-PCR may be conducted on a 1% agarose gel and then imaged using ultraviolet light.

TABLE 1

| Primary Antibody | Dilution | Source | Supplier |
| --- | --- | --- | --- |
| Glial fibrillary acidic protein ("GFAP") | 1:50 | α rabbit | Zymed or Invitrogen |
| Hepatocyte growth factor receptor ("HGFR") | 1:500 | α rabbit | Santa Cruse Biochemical |
| Nestin | 1:200 | α mouse | Chemicon |
| Microtubule associated protein 5 ("MAP-5") | 1:1000 | α mouse | Sigma |
| Neurofilament-200 ("NF-200") | 1:2000 | α rabbit | Sigma |
| Vimentin | 1:500 | α mouse | DAKO |
| Recoverin | 1:2000 | α rabbit | Chemicon |
| Rhodopsin | 1:200 | α mouse | Chemicon |
| Index of proliferation ("Ki-67") | 1:100 | α mouse | NovoCastra Laboratories |
| Von Willebrand factor ("VWF") | 1:400 | α rabbit | DAKO |
| Ulex europaeus agglutinin-1 lectin ("UEA-1") | 1:250 | | Pierce Biologicals |
| Vascular endothelial growth factor receptor ("VEGFR2") | 1:50 | α mouse | Chemicon |
| Platelet/endothelial cell adhesion molecule-1 ("PECAM", "CD31") | 1:40 | α mouse | DAKO |
| Sodium-potassium ATPase ("NaKATPase") | 1:1 | | Hybrid oma provided through a gift |
| Cluster of differentiation 133 protein ("CD133") | 1:500 | mouse anti-human | Miltenyi Biotech |
| Cluster of differentiation 34 protein ("CD34") | 1:200 | mouse anti-human | DAKO |
| Leukocyte common antigen ("CD45") | 1:200 | mouse anti-human | DAKO |
| Neurofilament NF-h ("NF-h") | 1:2000 | α rabbit | Sigma |
| Neurofilament NF-m ("NF-m") | 1:2000 | α rabbit | Sigma |
| Microtubule associated protein 2 ("MAP-2") | 1:500 | mouse anti-mouse | Sigma |

TABLE 2

| Secondary Antibody | Dilution | Source | Supplier |
|---|---|---|---|
| Cyanine 2 ("Cy 2") | 1:100 | α mouse | Jackson Immunochemicals |
| Cyanine 2 ("Cy 2") | 1:100 | α rabbit | Jackson Immunochemicals |
| Cyanine 3 ("Cy 3") | 1:300 | α mouse | Jackson Immunochemicals |
| Cyanine 3 ("Cy 3") | 1:300 | α rabbit | Jackson Immunochemicals |

The extra-retinal ocular tissue is generally derived from a mammalian donor. As used herein, the terms "mammal" or "mammalian" refers to any mammal, preferably a mouse, rat, other rodent, rabbit, dog, cat, swine, cattle, sheep, horse, primate, or human. The donor can be a neonate, juvenile, or adult.

As used herein, the term "neonate" refers to a mammal that is newly born to about six months of age. As used herein, the term "juvenile" refers to a mammal of about six months of age to about eighteen years of age. As used herein, the term "adult" refers to an adult mammal of eighteen years of age or older.

In some embodiments, the extra-retinal tissue is stored in Optisol® media prior to dissociation.

In some embodiments of the method of the invention, the dissociating of the retinal cells from the extra-retinal ocular tissue comprises:
 (a) mincing extra-retinal ocular tissue;
 (b) mixing the extra-retinal ocular tissue with a solution of collagenase to form a suspension after the mincing; and
 (c) filtering the suspension through a mesh.

In some embodiments, the method of isolating the retinal stem cells further comprises washing the extra-retinal ocular tissue with a saline solution prior to the mincing. In some embodiments, the saline solution is a phosphate buffered saline solution comprising penicillin and streptomycin.

In some embodiments, the solution of collagenase comprises about 0.01% to about 1% collagenase by weight. In some embodiment, the solution of collagenase comprises about 0.1% collagenase by weight.

As used herein, the term "about" means + or −10% of the value.

In some embodiments, the method of isolating the retinal stem cells further comprises warming the solution of collagenase from about 33° C. to about 40° C. In some embodiments, the mixing is carried out from about 10 to about 30 minutes. Preferably, the mixing is carried out for about 20 minutes. In some embodiments, the mixing is carried out for at least 5 minutes, at least 10 minutes, at least 15 minutes, at least 20 minutes, at least 30 minutes, or at least 40 minutes.

In some embodiments, the mesh has a size of about 50 μm to about 100 In some embodiments, the mesh has a size of about 50 μm, about 60 μm, about 70 μm, about 80 μm, about 90 μm, or about 100 μm. In some embodiments, the mesh has a size of about 70 μm.

In another aspect, the present invention provides an adult retinal stem cell line isolated from extra-retinal ocular tissue. Adult stem cells have traditionally been difficult to propagate and use for transplantation because, unlike embryonic cells, they have a self-limited life span. We have shown that, unlike traditional adult stem cells, our isolated cell lines have shown the ability to self renew indefinitely.

As used herein, the term "cell line" refers to cells of a single type taken from a mammal and grown in the laboratory for several passages.

As used herein, the term "adult retinal stem cells" refers to stem cells of non-embryonic origin, derived from an neonate, juvenile, or adult mammal.

In some embodiments, the adult retinal stem cells have the ability to differentiate into neuronal cells. In some embodiments, the adult retinal stem cells have the ability to differentiate into retinal ganglion cells. In some embodiments, the adult retinal stem cells have the ability to differentiate into retinal cells.

In some embodiments, the adult retinal stem cells isolated from vestigial tissue dissected from the eye of a donor mammal suffering from persistent fetal vasculature have the ability to differentiate into neuronal cells. In some embodiments, the adult retinal stem cells isolated from vestigial tissue dissected from the eye of a donor mammal suffering from persistent fetal vasculature have the ability to differentiate into retinal ganglion cells.

In some embodiments, the extra-retinal ocular tissue is a vestigial tissue dissected from the eye of a donor mammal suffering from persistent fetal vasculature, a neovascular membrane dissected from the eye of a donor mammal suffering from retinopathy of prematurity, or a pupillary membrane dissected from the eye of the donor mammal suffering from an inflammatory condition.

In some embodiments, the adult retinal stem cells express nestin, microtubule associated protein-5, neurofilament-200, or sodium-potassium ATPase.

In some embodiments, the adult retinal stem cells express nestin.

In some embodiments, the adult retinal stem cells express microtubule associated protein-5.

In some embodiments, the adult retinal stem cells express neurofilament-200.

In some embodiments, the adult retinal stem cells express sodium-potassium ATPase.

In some embodiments, the extra-retinal tissue was obtained from a neonate, juvenile, or adult. In some embodiments, the extra-retinal tissue was obtained from a human. In some embodiments, the extra-retinal tissue was obtained from an adult human.

In some embodiments, the adult retinal stem cell line is further capable of integrating into and repopulating a diseased retina.

In some embodiments, the adult retinal stem cell line is further capable of integrating into and repopulating the optic nerve.

In some embodiments, the adult retinal stem cells have survived in a culture medium for a period of about three months or greater.

The present invention further provides adult retinal stem cells isolated from vestigial tissue dissected from the eye of a donor mammal suffering from persistent fetal vasculature. In some embodiments, the adult retinal stem cells do not express photoreceptor markers in culture. In some embodiments, the adult retinal cells do not express rhodopsin and recoverin in culture.

A medium for the culturing of the retinal stem cells is described herein. Different materials, e.g., antifungal and antibacterial agents, can be added as deemed appropriate.

A culture medium for growing or maintaining adult retinal stem cells comprising:
 a serum-free culture medium;
 a first growth factor comprising from about 0.1 ng/mL to about 40 rig/mL of the serum-free culture medium;
 a second growth factor comprising from about 0.1 ng/mL to about 40 ng/mL of the serum-free culture medium;

a first neural supplement for enhancing neuronal progenitor cell growth comprising from about 0.1% v/v to about 10% v/v of the total culture medium;

optionally, a second neural supplement for enhancing neuronal progenitor cell growth comprising from about 0.1% v/v to about 10% v/v of the total culture medium; and optionally, a high-grade of heat-inactivated serum comprising from about 0.1% v/v to about 20% v/v of the total culture medium;

provided that the culture medium does not comprise neuroprogenitor cell-conditioned medium.

As used herein, the term "% v/v" refers percentage by volume. For example, 1% v/v is equivalent to 1 part volume per every 100 part volume of the total culture medium.

In some embodiments:

the first growth factor comprises from about 10 ng/mL to about 30 ng/mL of the culture medium;

the second growth factor comprises from 10 ng/mL to about 30 ng/mL of the culture medium;

the first neural supplement comprises from about 0.5% v/v to about 3% v/v of the total culture medium;

the optional second neural supplement, when present, comprises from about 0.5% v/v to about 3% v/v of the total culture medium; and the optional high-grade of heat-inactivated serum, when present, comprises from about 5% v/v to about 15% v/v of the total culture medium.

In some embodiments, the serum-free culture medium is X-VIVO 15 serum-free medium.

In some embodiments, the first growth factor is recombinant human, epidermal growth-factor (hrEGF), recombinant human, fibroblast growth factor-2 (hrFGF-2), or platelet-derived growth factor (PDGF). Recombinant human, fibroblast growth factor-2 (hrFGF-2) is also known as basic fibroblast growth factor (bFGF). In some embodiments, the first growth factor is recombinant human, fibroblast growth factor-2 (hrbFGF-2).

In some embodiments, the second growth factor is recombinant human, epidermal growth factor (hrEGF), recombinant human, fibroblast growth factor-2 (hrFGF-2), or platelet-derived growth factor (PDGF). In some embodiments, the second growth factor is recombinant human, epidermal growth factor (hrEGF).

In some embodiments, the first neural supplement is N-2 supplement (Gibco, Invitrogen®) or B-27 supplement (Gibco, Invitrogen®). In some embodiments, the first neural supplement is N-2 supplement. N-2 supplement contains 500 µg/mL insulin, 10 mg/mL h-transferrin, 0.63 µg/mL progesterone, 1.611 mg/mL putrascine, and 032 µg/mL selenite. In some embodiments, the first neural supplement is B-27 supplement.

In some embodiments, the optional second neural supplement, if present, is N-2 supplement or B-27 supplement. In some embodiments, the optional second neural supplement, if present, is B-27 supplement. In some embodiments, optional second neural supplement, if present, is N-2 supplement.

In some embodiments, the optional high-grade of heat-inactivated serum is fetal bovine serum.

In some embodiments:

the serum-free culture medium is X-VIVO 15 serum-free medium;

the first growth factor is recombinant human, fibroblast growth factor-2 (hrFGF-2);

the second growth factor is recombinant human, epidermal growth factor (hrEGF);

the first neural supplement is B-27 serum-free supplement;

the optional second neural supplement, when present, is N-2 serum-free supplement; and the optional high-grade of heat-inactivated serum, when present, is fetal bovine serum.

In some embodiments, the optional second neural supplement is present. In some embodiments, the optional high-grade of heat-inactivated serum is present. In some embodiments, the optional second neural supplement and optional high-grade of heat-inactivated serum are each present.

In some embodiments, in place of N-2 supplement, the culture medium comprises insulin, h-transferrin, progesterone, putrascine, and selenite.

In some embodiments:

the insulin comprises from about 100 µg/mL to about 1000 µg/mL of the total culture medium;

the h-transferrin comprises from about 0.1 mg/mL to about 100 mg/mL of the total culture medium;

the progesterone comprises from about 0.1 µg/mL to about 10 µg/mL of the total culture medium;

the putrascine comprises from about 0.1 mg/mL to about 10 mg/mL of the total culture medium; and the selenite comprises from about 0.01 µg/mL to about 10 µg/mL of the total culture medium.

In some embodiments:

the insulin comprises from about 300 µg/mL to about 700 µg/mL of the total culture medium;

the h-transferrin comprises from about 5 mg/mL to about 15 mg/mL of the total culture medium;

the progesterone comprises from about 0.3 µg/mL to about 0.9 µg/mL of the total culture medium;

the putrascine comprises from about 1 mg/mL to about 2 mg/mL of the total culture medium; and the selenite comprises from about 0.2 µg/mL to about 1 µg/mL of the total culture medium.

In one embodiment, the culture medium for growing or maintaining retinal stem cells comprises:

X-VIVO 15 serum-free medium;

recombinant human, fibroblast growth factor-2 (hrFGF-2) comprising about 20 ng/mL of the X-VIVO 15 serum-free medium;

recombinant human, epidermal growth factor (hrEGF) comprising about 20 ng/mL of X-VIVO 15 serum-free medium;

B-27 neural supplement comprising about 2% v/v of the total culture medium;

N-2 neural supplement comprising about 1% v/v of total culture medium; and, optionally, high-grade fetal bovine serum comprising about 10% of the total culture medium. The serum is added to induce differentiation of the cells.

The present invention further provides a method for maintaining adult retinal stem cells ("ARSC") in culture. Any of the culture media described herein, or any suitable combination or subcombination of embodiments of the culture media, can be used in the method of maintaining the adult retinal stem cells in culture.

The present invention further provides a method of treating a dystrophic eye of a mammal by administering ARSC as described herein. In some embodiments, the method comprises introducing autologous adult retinal stem cells into an eye of a mammal. As used herein, "autologous retinal stem cells" refer to retinal stem cells previously isolated from tissues dissected from the intended mammalian recipient.

The present invention further provides a method of treating a dystrophic eye of a mammal, comprising introducing adult retinal stem cells, isolated from vestigial tissue dissected from the eye of a donor mammal suffering from persistent fetal vasculature, into the eye of the mammal.

The methods can be used advantageously to repopulate or to rescue a dystrophic ocular tissue, particularly a dysfunctional retina. Retinal dysfunction encompasses any lack or loss of normal retinal function, whether due to disease, mechanical, or chemical injury, or a degenerative or pathological process involving the recipient's retina. The retinal stem cells may be injected or otherwise placed in a retinal site, the subretinal space, vitreal cavity (including injection or other introduction into the vitreous of the vitreal cavity), or the optic nerve, according to techniques known in the art. This includes the use of a biodegradable substrates as a carrier for the retinal stem cells. In some embodiments, the retinal stem cells are introduced into a retinal site, a subretinal space, an optic nerve, a vitreal cavity, a brain or a spinal cord.

The methods can be used to treat a mammalian recipient suffering from a lack or diminution of photoreceptor cell function. Examples of retinal dysfunction that can be treated by the adult retinal stem cell lines and methods of the invention include but are not limited to: photoreceptor degeneration (as occurs in, e.g., hereditary or acquired retinitis pigmentosa, cone dystrophies, cone-rod and/or rod-cone dystrophies, and macular degeneration, including age-related and early onset macular degeneration); retinal detachment and retinal trauma; photic lesions caused by laser or sunlight; a macular hole; a macular edema; night blindness and color blindness; ischemic retinopathy as caused by diabetes or vascular occlusion; retinopathy due to prematurity/premature birth; infectious conditions, such as, e.g., CMV (cytomegalovirus) retinitis, herpes type 1 retinitis, Ebstein-Barr virus retinitis, toxoplasmosis, rubella and pox virus; inflammatory conditions, such as the uveitidies, multifocal choroiditis and uveitis, birdshot chorioretinopathy, collagen vascular diseases affecting the posterior segment of the eye, including Wegener's granulomatosis, uveitis associated with systemic lupus erythematosus, uveitis associated with polyarteritis nodosa, peripheral or intermediate uveitis, chronic central serous chorioretinopathy, and myopic choroidal neovascular membranes and scars. Inflammatory disorders also include Behçet syndrome, intermediate uveitis (pars planitis), masquerade syndromes, peripheral uveitis, ocular syphilis, ocular tuberculosis, viral-related chorioretinitis (ARN) syndrome, HIV-related uveitis, progressive outer retinal necrosis syndrome, sympathetic ophthalmia, white dot syndromes, presumed ocular histoplasmosis syndrome, acute macular neuroretinopathy, diffuse unilateral subacute neuroretinitis, ophthalmomyiasis, serpiginous choroidopathy, panuveitis, birdshot retinochoroidopathy, and uveitis associated with disorders such as juvenile rheumatoid arthritis, Kawasaki syndrome, multiple sclerosis, sarcoidosis, toxocariasis, toxoplasmosis, Vogt-Koyanagi-Harada (VKH), and HLA-B27 seropositive spondylopathy syndromes.

Other disorders include tumors, such as retinoblastoma and ocular melanoma. Additionally, the ARSCs can be used for replacement of inner retinal neurons, which are affected in ocular neuropathies including glaucoma, traumatic optic neuropathy, degenerative optic neuropathy, ischemic optic neuropathy, optic neuropathy from multiple sclerosis, and radiation optic neuropathy and retinopathy.

The methods can also be used to treat optic nerve diseases such as optic atrophy, ischemic optic neuropathy, diabetes induced optic atrophy, optic nerve hypoplasia, morning glory syndrome, Graves ophthalmopathy, optic neuritis, cytomegalovirus neuritis, arteritic optic neuropathy, compressive neuropathy, diabetic neuropathy, giant cell arteritis, infiltrative neuropathy, nutriotional, ischemic neuropathy, retrobulbar optic neuritis, retrobulbar ischemic neuropathy, toxic neuropathy, traumatic neuropathy; optic nerve diseases resulting from causes such as syphilis, Lyme disease, toxoplasmosis, cat scratch disease, systemic lupus erythematosus, paraneoplastic syndrome, multiple sclerosis, and autoimmune disease; degenerative optic diseases such as age-related macular degeneration, early onset macular degeneration, Usher Syndrome, retinitis pigmentosa, cone-road dystrophy, and choroideremia; and congenital optical diseases such as Leber's congential amaurosis, congential stationary night blindness, and optic nerve hypoplasia.

One of skill in the art will recognize that there is overlap between the various classifications of the disorders and conditions listed herein.

Other examples of retinal dysfunction that can be treated by use of the stem cells and methods of the invention are well-known to one of ordinary skill in the art, and may be found in, e.g., van der Kooy et al., U.S. Pat. No. 6,117,675 (issued September 2000), or PCT International Application No. PCT/US00/03534, which relates to integration of transplanted neural progenitor cells of non-retinal origin, into neural tissue of immature dystrophic recipients, each of which are incorporated by reference in their entireties.

In some embodiments, the dystrophic eye is a result of photoreceptor degeneration, retinal detachment, retinal trauma, a photic lesion, a macular hole, a macular edema, night blindness, color blindness, ischemic retinopathy, retinopathy due to premature birth, infection, inflammatory condition, or an ocular neuropathy. In some embodiments, the dystrophic eye is a result of a tumor, a degenerative optic disease, or a congenital optical disease.

In some embodiments, the dystrophic eye is a result of an ocular neuropathy. In some embodiments, the optic neuropathy is glaucoma, traumatic optic neuropathy, degenerative optic neuropathy, ischemic optic neuropathy, optic neuropathy from multiple sclerosis, or radiation optic neuropathy, or retinopathy.

In some embodiments, the dystrophic eye is the result of multifocal choroiditis, birdshot chorioretinopathy, collagen vascular diseases affecting the posterior segment of the eye, Wegener's granulomatosis, peripheral uveitis, intermediate uveitis, chronic central serous chorioretinopathy, myopic choroidal neovascular membranes, myopic choroidal neovascular membranes scars, Behçet syndrome, a masquerade syndrome, ocular syphilis, ocular tuberculosis, viral-related chorioretinitis (ARN) syndrome, HIV-related uveitis, progressive outer retinal necrosis syndrome, sympathetic ophthalmia, a white dot syndrome, presumed ocular histoplasmosis syndrome, acute macular neuroretinopathy, diffuse unilateral subacute neuroretinitis, ophthalmomyiasis, serpiginous choroidopathy, panuveitis, birdshot retinochoroidopathy, uveitis associated with juvenile rheumatoid arthritis, uveitis associated with Kawasaki syndrome, uveitis associated with multiple sclerosis, uveitis associated with sarcoidosis, uveitis associated with toxocariasis, uveitis associated with toxoplasmosis, uveitis associated with systemic lupus erythematosus, uveitis associated with polyarteritis nodosa, uveitis associated with Vogt-Koyanagi-Harada, or uveitis associated with a HLA-B27 seropositive spondylopathy syndrome.

In some embodiments, the dystrophic eye is the result of optic atrophy, ischemic optic neuropathy, diabetes induced optic atrophy, optic nerve hypoplasia, morning glory syndrome, Graves ophthalmopathy, optic neuritis, cytomegalovirus neuritis, arteritic optic neuropathy, compressive neuropathy, diabetic neuropathy, giant cell arteritis, infiltrative neuropathy, nutriotional, ischemic neuropathy, retrobulbar optic neuritis, retrobulbar ischemic neuropathy, toxic neuropathy, or traumatic neuropathy.

In some embodiments, the dystrophic eye is the result of an optic nerve disease associated with syphilis, Lyme disease, toxoplasmosis, cat scratch disease, systemic lupus erythematosus, paraneoplastic syndrome, multiple sclerosis, or autoimmune disease.

In some embodiments, the dystrophic eye is the result of age-related macular degeneration, early onset macular degeneration, Usher Syndrome, retinitis pigmentosa, choroideremia, cone dystrophy, cone-rod dystrophy, rod-cone dystrophy, Leber's congenital amaurosis, congenital stationary night blindness, Sticklers Syndrome, colobomas, vitreoretinal dysplasia, achromatopsia, or optic nerve hypoplasia.

In some embodiments, the inflammatory condition is multifocal choroiditis, birdshot chorioretinopathy, collagen vascular diseases affecting the posterior segment of the eye, Wegener's granulomatosis, peripheral uveitis, intermediate uveitis, chronic central serous chorioretinopathy, myopic choroidal neovascular membranes, myopic choroidal neovascular membranes scars, Behçet syndrome, a masquerade syndrome, ocular syphilis, ocular tuberculosis, viral-related chorioretinitis (ARN) syndrome, HIV-related uveitis, progressive outer retinal necrosis syndrome, sympathetic ophthalmia, a white dot syndrome, presumed ocular histoplasmosis syndrome, acute macular neuroretinopathy, diffuse unilateral subacute neuroretinitis, ophthalmomyiasis, serpiginous choroidopathy, panuveitis, or birdshot retinochoroidopathy.

In some embodiments, the inflammatory condition is uveitis associated with a disorder selected from the group consisting of juvenile rheumatoid arthritis, Kawasaki syndrome, multiple sclerosis, sarcoidosis, toxocariasis, toxoplasmosis, systemic lupus erythematosus, polyarteritis nodosa, Vogt-Koyanagi-Harada (VKH), or a HLA-B27 seropositive spondylopathy syndrome.

In some embodiments, the infection is cytomegalovirus retinitis, herpes type 1 retinitis, Ebstein-Barr virus retinitis, toxoplasmosis, rubella, or pox virus.

In some embodiments, the optic nerve disease is optic atrophy, ischemic optic neuropathy, diabetes induced optic atrophy, optic nerve hypoplasia, morning glory syndrome, Graves ophthalmopathy, optic neuritis, cytomegalovirus neuritis, arteritic optic neuropathy, compressive neuropathy, diabetic neuropathy, giant cell arteritis, infiltrative neuropathy, nutriotional, ischemic neuropathy, retrobulbar optic neuritis, retrobulbar ischemic neuropathy, toxic neuropathy, or traumatic neuropathy.

In some embodiments, the optic nerve disease results from a cause selected from the group consisting of syphilis, Lyme disease, toxoplasmosis, cat scratch disease, systemic lupus erythematosus, paraneoplastic syndrome, multiple sclerosis, and autoimmune disease.

In some embodiments, the degenerative optic disease is the result of age-related macular degeneration, early onset macular degeneration, Usher Syndrome, retinitis pigmentosa, cone-road dystrophy, or choroideremia.

In some embodiments, the congenital optic disease is Leber's congenital amaurosis, congenital stationary night blindness, or optic nerve hypoplasia.

In some embodiments, the tumor is retinoblastoma or ocular melanoma.

In some embodiments, the dystrophic eye is the result of glaucoma.

In using the adult retinal stem cells to treat retinal dysfunction, one can, in conjunction with introducing the retinal stem cells into a recipient's eye, administer a substance that stimulates differentiation of the neuroretina-derived stem cells into photoreceptors cells or other retinal cell types (e.g., bipolar cells, ganglion cells, horizontal cells, amacrine cells, Mueller cells). When ARSCs are introduced to treat a neural dysfunction of the eye, one can also utilize a substance (or combination of substances) that stimulates differentiation of the neuroretina-derived stem cells into neurons, astrocytes, or oligodendrocytes.

In some embodiments, the method of treating a dystrophic eye further comprises administering to the mammalian recipient, a substance that stimulates differentiation of the adult retinal stem cells into photoreceptors cells.

In some embodiments, the method of treating a dystrophic eye further comprises administering to the mammalian recipient, a substance that stimulates differentiation of the adult retinal stem cells into neurons.

In some embodiments, the method of treating a dystrophic eye further comprises administering to the mammalian recipient, a substance that stimulates differentiation of the adult retinal stem cells into astrocytes In some embodiments, the method of treating a dystrophic eye further comprises administering to the mammalian recipient, a substance that stimulates differentiation of the adult retinal stem cells into oligodendrocytes.

In some embodiments, the recipient is a neonate, juvenile, or adult. In some embodiments, the recipient is a human.

In some embodiments, the present invention provides a method of replenishing retinal ganglion cells comprising introducing the adult retinal stem cells into the eye of the mammal, wherein the adult retinal stem cells are isolated from vestigial tissue dissected from the eye of a donor mammal suffering from persistent fetal vasculature.

In some embodiments, the present invention provides a method of replenishing retinal ganglion cells comprising introducing autologous adult retinal stem cells into the eye of the mammal.

The present invention further provides use of adult stem cells isolated from vestigial tissue dissected from the eye of a donor mammal suffering from persistent fetal vasculature for use in a method of treating a dystrophic eye of a mammal. The present invention also provides adult stem cells isolated from vestigial tissue dissected from the eye of a donor mammal suffering from persistent fetal vasculature for use in a method of treating a dystrophic eye of a mammal. The adult retinal stem cells can be used in any of the methods in the embodiments described herein.

The present invention further provides use of autologous retinal stem cells in a method of treating a dystrophic eye of a mammal. The present invention also provides autologous retinal stem cells for use in a method of treating a dystrophic eye of a mammal.

The autologous retinal stem cells can be used in any of the methods in the embodiments described herein.

The present invention further provides a kit for harvesting extra-retinal ocular tissue comprising a sterile container and a harvesting solution, wherein the kit allows the survival of the tissue until later dissociation of cells from the tissue. The kits of the present invention can be used to store the extra-ocular tissue after dissection until a later time when the ARSCs of the invention can be dissociated from the tissue. The kits of the present invention are also useful for transporting the tissue to another location where the dissociation of the ARSCs may take place.

As used herein, the term "harvesting solution" refers to any solution suitable for preserving ocular tissue. The harvesting solution may be a commercially available solution, or may be separately prepared from a serum-free tissue culture medium. Any serum-free tissue culture medium suitable for preserving ocular tissue may be used in the kits of the invention.

In some embodiments, the harvesting solution is a solution suitable for preserving corneal tissue. In some embodiments, the harvesting solution is Optisol.

In some embodiments, the harvesting solution is X-VIVO serum-free medium.

In some embodiments, the harvesting comprises an antibiotic component. As used herein, the term "antibiotic component" refers to a single antibiotic or a combination of two or more antibiotics. In some embodiments, the antibiotic combination comprises penicillin, streptomycin, or gentamicin, or a combination thereof. In some embodiments, the antibiotic component comprises penicillin and streptomycin. In some embodiments, the antibiotic component comprises penicillin and gentamicin. In some embodiments, the harvesting solution comprises X-VIVO serum-free medium and an antibiotic component comprising penicillin, streptomycin, or gentamicin or a combination thereof.

In some embodiments, the harvesting solution comprises three times the normal dosage of antibiotics. In some embodiments, the harvesting solution comprises 300 IU/mL of a combination of penicillin and streptomycin, such as that available from Gibco, Invitrogen. In some embodiments, the harvesting solution comprises 300 IU/mL of penicillin and 150 µg/mL of gentamicin. As used herein, the abbreviation "IU/mL" refers to international units of the antibiotic per mL of harvesting solution.

In some embodiments, the kit allows the survival of the tissue for up to about 7 days. In some embodiments, the kit allows the survival of the tissue for up to about 4 days. In some embodiments, the kit allows the survival of the tissue for up to about 2 days. As used herein, the term "survival" indicates that the condition of the tissue is such that retinal stem cells can still be isolated from the tissue.

In some embodiments, the harvested extra-retinal ocular tissue is a vestigial tissue dissected from the eye of a donor mammal suffering from persistent fetal vasculature, a neovascular membrane dissected from the eye of a donor mammal suffering from retinopathy of prematurity, or a pupillary membrane dissected from the eye of the donor mammal suffering from an inflammatory condition.

Any sterile container can be used with the kits of the invention, including sterile vials and ampoules. In some embodiments, the sterile container comprises two or more collection vessels. in some embodiments, the two or more collection vessels are separate sterile compartments within one container, allowing the preservation of different samples of extra-ocular tissue in each collection vessel with its own supply of harvesting solution.

Certain features of the invention which are, for clarity, described herein in the context of separate embodiments, can also be provided in combination in a single embodiment. Conversely, various features of the invention which are, for brevity, described in the context of a single embodiment, can also be provided separately or in any suitable subcombination.

In order that the invention disclosed herein may be more efficiently understood, examples are provided below. It should be understood that these examples are for illustrative purposes only and are not to be construed as limiting the invention in any manner.

EXAMPLES

Example 1

Isolation of Retinal Stem Cells from Human PFV Membrane

During surgical repair of the eyes of a human patient with PFV, the PFV membrane was carefully dissected from the underlying retina and neighboring ocular structures, such as the ciliary body, and was removed en bloc. The dissected PFV membrane was placed in Optisol® media (Bausch & Lomb) for transport to the laboratory.

Upon receipt of the PFV membrane, it was first washed in phosphate buffered saline ("PBS") containing 3× antibiotics (penicillin-streptomycin 300 µg/ml). The membrane was then finely minced, collected into a centrifuge tube, pelleted at 1200 rpm and resuspended in 0.1% Type, 1 collagenase which had been pre-warmed to 37° C. Tissue in collagenase was transferred to a receptacle containing a stir bar and agitated for twenty minutes after which time the supernatant was forced through a 70 µm mesh. The resulting suspension was pelleted and immediately seeded into 24 mm plastic (uncoated) tissue culture wells containing the culture medium of Table 3. Alternatively, cells were seeded into a culture medium similar to that of Table 3 except that either the fetal bovine serum or Amphotericin B were not included. Fresh collagenase was added to the remaining tissue and the above cycle repeated until all tissue was digested. Cells were grown at 37° C. under routine conditions of 95% air:5% carbon dioxide at cell concentrations of $1\times10^4$ to $5\times10^5$ cells/mL.

These cells were maintained or frozen at −150° C., or maintained in culture. When frozen, the cells were placed in a cell freezing medium consisting of 40% by volume of the culture medium of Table 3, 50% by volume of Cyroprotective Medium (Cambrex Corp.), and 10% by volume of additional fetal bovine serum. The cells were placed in this medium at a density of $1\times10^6$ cells per 1 ml of cell freezing medium in a cryoprotective vial. The cyroprotective vials were bathed in isopropyl alcohol and placed in the −80° C. freezer, in order to cool the vials at a rate of approximately 1° C. per minute. After cooling in isopropyl alcohol, the vials were placed in a −80° C. freezer overnight. The frozen vials were then placed in a liquid $N_2$ freezer in designated boxes.

A sample of the cell line was deposited with the American Type Culture Collection 10801 University Boulevard, Manassas, Va. 20110-2209, on May 2, 2006 (Patent Deposit Designation PTA-7564).

TABLE 3

| Material | Concentration |
| --- | --- |
| X-VIVO ™ serum-free medium (Cambrex Corp.) | |
| Fetal bovine serum | 10% v/v[a] |
| recombinant human basic fibroblast growth factor (hrFGF) | 20 ng/mL[b] |
| recombinant human epidermal growth factor (hrEGF) | 20 ng/mL[b] |
| N-2 neural supplement | 1% v/v[a] |
| B-27 neural supplement | 2% v/v[a] |
| Amphotericin B | 0.25 µg/mL[c] |

[a] units of % v/v indicates percent by volume based upon the total culture medium
[b] units of ng/mL indicate nanograms per 1 mL of X-VIVO ™ serum-free medium
[c] units of µg/mL indicate micrograms per 1 mL of total culture medium Example 2

Isolation of Retinal Stem Cells from Neovascular Tissue from Eyes with Advanced Retinopathy of Prematurity (ROP)

During surgical repair of the eyes of a human patient with advanced stage 4 or stage 5 retinopathy of prematurity (ROP), the neurovascular membrane was carefully dissected from the underlying detached retina was removed en bloc. The dissected neurovascular membrane was placed in Optisol® media for transport to the laboratory.

Upon receipt of the neurovascular membrane, it was first washed in PBS containing 3× antibiotics (penicillin-streptomycin 300 µg/ml). The membrane was then finely minced, collected into a centrifuge tube, pelleted at 1200 rpm and resuspended in 0.1% Type 1 collagenase which had been pre-warmed to 37° C. Tissue in collagenase was transferred to a receptacle containing a stir bar and agitated for twenty minutes after which time the supernatant was forced through a 70 µm mesh. The resulting suspension was pelleted and immediately seeded into 24 mm plastic (uncoated) tissue culture wells containing the culture medium of Table 3. Fresh collagenase was added to the remaining tissue and the above cycle repeated until all tissue was digested. Cells were grown at 37° C. under routine conditions of 95% air:5% carbon dioxide at cell concentrations of $1\times10^4$ to $5\times10^5$ cells.

Example 3

Isolation of Retinal Stem Cells from Pupillary Membranes Arising from Inflammatory Conditions During surgical repair of the eyes of human patients with pupillary membranes arising from an inflammatory condition, the pupillary membrane was carefully dissected from the underlying detached retina was removed en bloc. The dissected pupillary membrane was placed in Optisol® media for transport to the laboratory.

Upon receipt of the pupillary membrane, it was first washed in PBS containing 3× antibiotics (penicillin-streptomycin 300 µg/ml). The membrane was then finely minced, collected into a centrifuge tube, pelleted at 1200 rpm and resuspended in 0.1% Type 1 collagenase which had been pre-warmed to 37° C. Tissue in collagenase was transferred to a receptacle containing a stir bar and agitated for twenty minutes after which time the supernatant was forced through a 70 µm mesh. The resulting suspension was pelleted and immediately seeded into 24 mm plastic (uncoated) tissue culture wells containing the culture medium of Table 3. Fresh collagenase was added to the remaining tissue and the above cycle repeated until all tissue was digested. Cells were grown at 37° C. under routine conditions of 95% air:5% carbon dioxide at cell concentrations of $1\times10^4$ to $5\times10^5$ cells.

Example 4

Propagation of Retinal Stem Cells in Culture

We have found that, using our specially developed medium, the retinal stem cells we have isolated were able to propagate in culture for at least three months, through 10 cell passages. Briefly, the cells were plated at $2\times10^5$ cells/mL in T-75 flasks or 100 mm culture dishes in the cell medium of Table 3.

Example 5

Cells Isolated from Human PFV Membrane and Grown Under Tissue Culture Conditions Exhibit Characteristics of Retinal Stem Cells Immunocytochemistry (ICC) and reverse-transcriptase polymerase chain reaction (RT-PCR) were used to study retinal stem cells isolated from PFV as in Example 1. Various markers were studied with selected antibodies or by RT-PCR, including neuroglial expression markers (vimentin; neurofilament-200 ("NF-200"); microtubule associated protein 2+5 ("MAP"2+5); and glial fibrillary acidic protein ("GFAP")); endothelial expression markers (platelet/endothelial cell adhesion molecule-1 ("PECAM", "PECAM-1", or "CD31")); vascular vascular expression markers (vascular endothelial growth factor receptor 2 ("VEGFR2") and hepatocyte growth factor receptor ("HGFR")); photoreceptor markers (recoverin and rhodopsin); neuronal expression markers (microtubule associated protein ("MAP-5"); and progenitor cell expression markers (nestin). Additionally, ICC was used to study the index of proliferation ("Ki-67").

For ICC, retinal stem cells were grown in the culture medium of Example 1 with or without added fetal bovine serum on glass coverslips or chamber slides coated with various substances, including collagen, fibronectin, lamenin, or 1% gelatin. The cells were fixed in 4% paraformaldehyde for 30 minutes at room temperature. The cells were then washed three times with PBS. The cells were then blocked and permeabilized in PBS containing 1% Bovine Serum Albumin and 0.2% Triton X-100 for 30 minutes at room temperature. The cells were then incubated with primary antibody for 1.5 to 2 hours at room temperature or overnight at 4° C., followed by rinsing three times with PBS for 10 minutes per rinse. The cells were then incubated with secondary antibody for 1 hour at room temperature, followed by rinsing three times with PBS for 10 minutes per rinse. The cells were then visualized using a fluorescence microscope. The antibody diluent was PBS containing 1% Bovine Serum Albumin. Typical primary and secondary antibodies that are useful for the ICC studies of these markers are summarized in Tables 1 and 2.

For RT-PCR, tissue and cell samples were extracted using a combination of Trizol and column purification (RNAqueous, Ambion) procedures. Following DNase treatment (Promega), 200 ng samples of RNA were used in a two-stage RT-PCR with Quantitect reverse transcriptase (Qiagen) and oligo-dT priming. Following this, PCR amplification was performed using 2× Power SYBR mix (Applied Biosystems; ABI). PCR was done on an ABI 7900HT real time thermocycler using cycling conditions according to manufacturers recommendations.

Primers were selected, as a subset of the antibody marker list used for immunochemical characterizations, using either the Primer3 (Broad Institute, MIT) or the Primer Express (ABI) design tools. Additional primer sets included MAPS RNA splice variant (mature neuronal marker), crystallin A and B (structural, molecular chaperones), and beta-actin (reference gene). Primers were then verified by Spidey mRNAigenomic DNA alignment and BLAST search. Primers were used at 100 nM concentration.

For real time PCR, threshold cycle values were collected, and these data were normalized against the threshold cycle values obtained in the same runs for endogenous control beta-actin RNA. Expression values were calculated using the dd-Ct method (ABI).

Results

Figure 2:
FIG. 2 depicts the formation of neurospheres by stem cells isolated from human PFV membrane and grown under tissue culture conditions.

During culturing, the cells were observed to form neurospheres in culture, a collection of stem cells adhered together to form a ball-like structure (FIGS. 1 and 2). Two types of cells were first observed in culture. The first type of cell was slender with long intertwining processes, while the second type of cell was rounder with small granular inclusions in its cytoplasm. The second cell type was lost through passaging, but the first cell type was retained.

Figure 3:
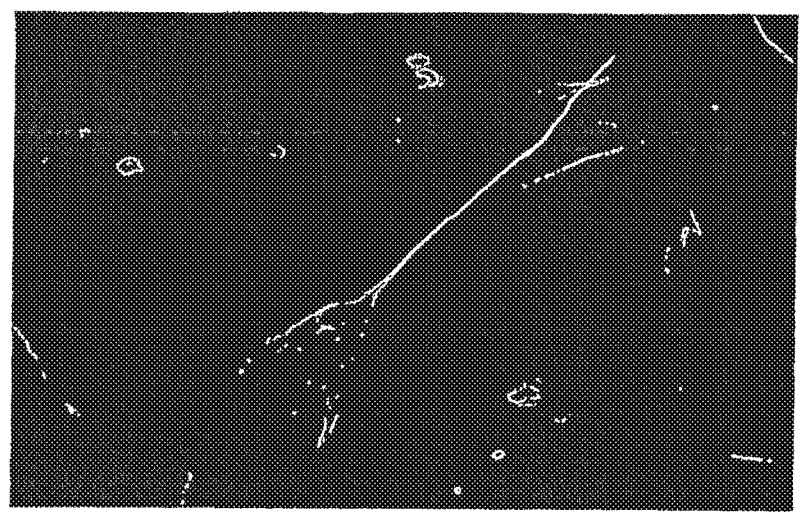
FIG. 3 depicts immunocytochemistry results showing the expression of nestin by cells isolated from human PFV membrane and grown under tissue culture conditions.
Figure 4:
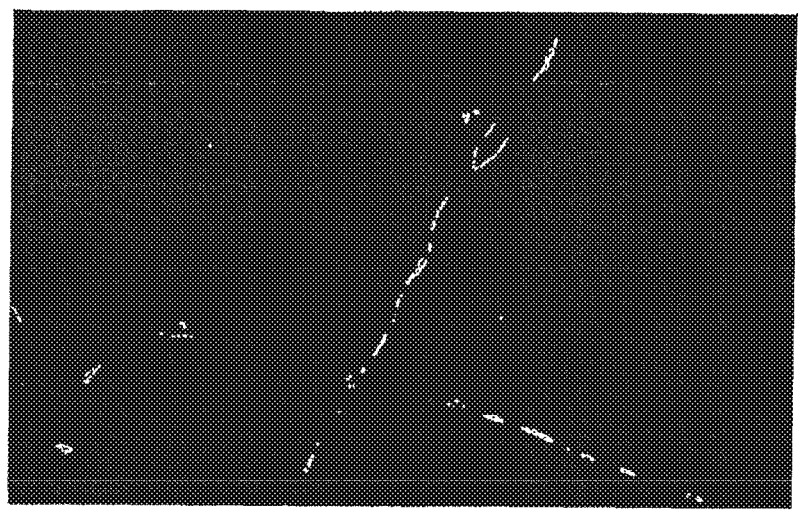
FIG. 4 depicts immunocytochemistry results showing the expression of microtubule associated protein-5 by cells isolated from human PFV membrane and grown under tissue culture conditions.
Figure 5:
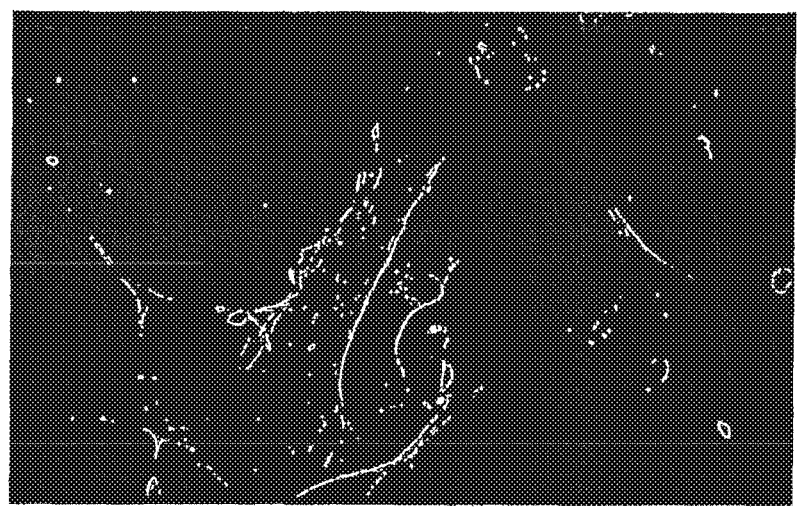
FIG. 5 depicts immunocytochemistry results showing the expression of neurofilament-200 (NF-200) by cells isolated from human PFV membrane and grown under tissue culture conditions.
Figure 6:
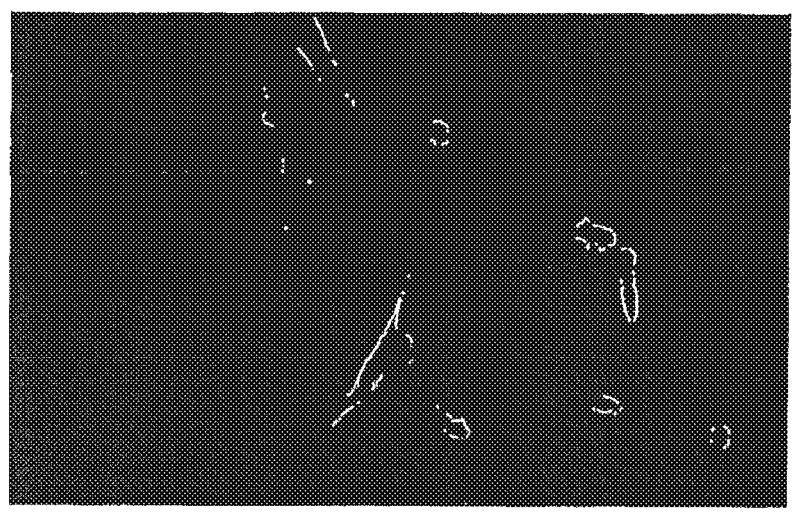
FIG. 6 depicts immunocytochemistry results showing the expression of sodium-potassium ATPase by cells isolated from human PFV membrane and grown under tissue culture conditions.

ICC indicated positive expression of the neural markers, neurofilament-200 (NF-200) and MAP2±5 (a combination of MAP-2 and MAP-5). Vimentin was also positive, but no expression of GFAP or PECAM was observed. ICC shows that the cells express markers associated with neuronal cells, including nestin (FIG. 3), microtubule associated protein-5 (MAP-5) (FIG. 4), neurofilament-200 (NF-200) (FIG. 5), and sodium-potassium NaKATPase, an electrolyte channel protein found in all cells including neuronal cells (FIG. 6). ICC also indicated positive expression of vimentin, but no expression of GFAP, PECAM, rhodopsin, or recoverin was observed.

PCR confirmed the presence of these markers and further indicated that cultures are mixtures of cell types. Cell populations contain relatively (versus actin controls) abundant MAPS and nestin RNAs, lower amounts of GFAP and NF-200 RNAs, and no detectable cluster differentiation 133 protein ("CD-133") or T-cell acute lymphocytic leukemia 1 ("Tal-1") RNAs.

Example 6

Characterization of Cells Isolated from ROP Tissue and Grown Under Tissue Culture Conditions Using the techniques summarized for Example 5, the retinal stem cells isolated as in Example 2 were studied using ICC and RT-PCR. ICC indicated positive expression of MAP-5, GFAP, VEGFR2, HGFR, nestin, and NF-200. The retinal stem cells were also positive for two photoreceptor markers, rhodopsin and recoverin, and displayed a positive index of proliferation (Ki-67).

RT-PCR indicated positive expression of MAP-5, GFAP, VEGFR2, HGFR, nestin, recoverin, rhodopsin, as well as a trace amount of PECAM (CD31).

Example 7

Characterization of Retinal Stem Cells from Pupillary Membranes

Using the techniques summarized for Example 5, ICC was used to show that the retinal stem cells isolated as in Example 3 express nestin.

Example 8

In vivo Integration of Adult Retinal Stem Cells Isolated from Neovascular Tissue from Eyes with Advanced Retinopathy of Prematurity (ROP)

Cells isolated from the neovascular tissue in eyes with ROP as in example 2 were transplanted into the subretinal space of SCID mice (devoid of immune system). Cells were introduced into the subretinal space by injecting between 2 to 3 microliters of X-VIVO™ serum-free medium containing between 50,000 to 100,000 cells using a small tapered glass needle that was passed through the sclera under direct retina observation. This technique ensures that the location of the needle is in fact in the subretinal space. Cells were tagged with a fluorescent marker. Mice were observed for between 2 to 14 days. Eyes were removed and processed for immunocytochemistry. The cells were found to have survived the environment of the subretinal space. These cells were able to differentiate into mature retinal elements. In particular, cells were noted to express neurofilament-200 (NF-200), a marker for differentiated neurons and recoverin, a photoreceptor marker. These experiments indicate that these cells are able to survive and proliferate within the subretinal space of mice and can be good candidates for retinal transplantation.

Example 9

ARSCs Transplanted into Chick Retina

Retrolental tissue was extracted from a patient with PFV. Cells were isolated using the procedure in Example 1 and grown in culture using the fetal bovine serum enriched culture medium of Example 1. Cells were labeled with PKH67 red fluorescent cell linker and transplanted onto retina explants derived from embryonic E8 chicks. Retinal explants were incubated between day 1 and day 8. Explants were collected, cyrosectioned, and immunostained for vimentin, neuronal/glial markers (nestin, NF-h, NF-m, and GFAP), endothelial markers (CD34, AC133 (CD133), CD31, and VEGFR2), and bone-marrow marker (CD45) using the techniques summarized in Example 5.

Strong vimentin expression was detected PFV cells in co-culture throughout the whole time course. In co-culture condition, these cells proliferated and penetrated the immature chick retina. These cells did not express any detectable endothelial or neuronal markers between days 1-3. On day 3/4, CD31 (PECAM) expressing cells were detected within the transplanted cells. Between days 3-5, NF-m+ expressing cells from the host retina extended axonal-like sprouts into the transplants.

Example 10

Autologous Transplantation

ARSCs are isolated from a donor with one of the conditions in Examples 1-3 using the procedures set forth therein. The isolated ARSCs are then cultured in the medium described above until sufficient numbers of ARSCs for transplantation back into the donor are obtained. The number will depend upon the type and severity of condition, and the donor, and is readily ascertainable by one of ordinary skill in the art. The ARSCs are then harvested from culture and transplanted back into the donor eye under sterile conditions. ARSCs are transplanted using standard PARS PLANA vitrectomy, during which time cells are introduced (injected) under the retina through a small retinotomy (hole). Alternatively, the ARSCs are placed over the retinal surface using standard surgical techniques.

Example 11

ARSCs Transplanted into C57BL/6 Mice

Retrolental tissue was extracted from a patient with PFV. Cells were isolated using the procedure in Example 1 and grown in culture using the fetal bovine serum enriched culture medium of Example 1. The cells were prelabeled with cell linker, PKH67, tagged with rhodamine, and transplanted into the vitreous of C57BL/6 mice and examined on days 3, 7, 10, 14, 28, and 56 (n=5 for each time point). Eyes were cyrosectioned and stained with a panel of markers including nestin, NFh (neural filament high), NFm (neural filament medium), NF-200, growth-associated protein-43 ("GAP-43"), phosphokinase C ("PKC")-α, PECAM, recoverin (photoreceptor constituent) and glial acidic fibrillary protein (GFAP).

All transplants survived the new environment of the recipient vitreous well and were able to be recovered at all time points. By day 3, GAP-43 was mainly found in the cell bodies, while NF-200 was detected in the neurites (see FIGS. 7(a) and (b), respectively), suggesting that some PFV cells had already begun to differentiate into neuronal cells. No GFAP, PKC-α and recoverin were detected.

On day 28, PFV cells formed an aggregate close to the retina. The aggregate linked with the optic nerve head (ONH) by a stalk-like structure (arrowhead) mainly built up by cells and neurites. Interestingly, no GFAP+ cells were found in the stalk-like structure. Instead, the cells were found in the stalk-like structure expressed high levels of NF-200 (see FIGS. 7(c) and (d)). GAP-43 was also expressed within axons in the stalk-like structure. GAP-43 expressing fibers extended into the optic nerve head and combined up with the host-fibers. On day 56, GAP-43 and NF-200 expression were down-regulated, although some fibers continued to strongly express NF-200 within the stalk-like structure (see FIGS. 7(e) and (f)). PKC-a expression was found but no GFAP or recoverin expression was found in the PFV aggregates on days 28 and 56.

These results demonstrate that ARSCs can differentiate into neuronal cells in vivo. This data also shows that the PFV cells survive in the mouse vitreous for up to 8 weeks. Further, the acceptance of the xenogeneic transplant (human PFV cells to mouse vitreous) implies that it may be safe for transplantation in an allogeneic condition (human PFV cells to human vitreous). These results also demonstrate that PFV neurons preferentially aim for and penetrate the optic nerve head, and not the retinal tissue. These observations suggest that there is a good likelihood that PFV axons can penetrate the optic nerve and follow the optic track.

Example 12

ARCs Transplanted into DBA/2J Mice

Retrolental tissue is extracted from a patient with PFV. Cells are isolated using the procedure in Example 1 and grown in culture using the fetal bovine serum enriched culture medium of Example 1. The PFV cells are then transplanted into the vitreous of DBA/J2J mice. DBA/J2J mice are chosen as a useful model for glaucoma and the further study of the rescue or replacement of retinal ganglion cells due to elevated intraocular pressure in glaucoma. For example, DBA/2J mice develop pigment dispersion, iris atrophy, anterior synechiae (adhesions between the iris and the lens), and elevated intraocular pressure. Loss of iris pigment epithelium is first observed in mice between the ages of 3 to 4 months. At 9 to 10 months of age, most animals show elevated intraocular pressure, active depletion of retinal ganglion cells, followed by optic nerve atrophy and cupping. The severity of these lesions is found to increase with age. It is thought that iris pigment dispersion is caused by premature stop codon mutation in the Gpnmb gene ($Gpnmb^{R150X}$) found only in DBA/2J mice that are homozygous for $Gpnmb^{R150X}$. Iris stromal atrophy is caused by the recessive Tyrp $I^b$ mutant allele in the same mouse. These characteristics indicate that DBA/2J mice present a useful model by which one can study the rescue or replacement of retinal ganglion cells due to elevated intraocular pressure in glaucoma.

This application claims the benefit of priority to International Patent Application No. PCT/US2006/017861, filed on May 3, 2006, which is hereby incorporated by reference in its entirety.

Various modifications of the invention, in addition to those described herein, will be apparent to those skilled in the art from the foregoing description. Such modifications are also intended to fall within the scope of the appended claims. Each reference cited in the present application, including patents, published applications, and journal articles, is incorporated herein by reference in its entirety.

What is claimed is:

1. A method of treating a dystrophic eye of a human, comprising introducing human adult retinal stem cells into the eye of said human, wherein
   said adult human retinal stem cells are isolated from vestigial tissue dissected from the eye of a donor human suffering from persistent fetal vasculature;
   said dystrophic eye comprises an optic neuropathy associated with glaucoma;
   said cells lacks rhodopsin or recoverin photoreceptor marker expression and differentiates into a neuronal cell, retinal ganglion cell, or retinal cell;
   said cells expresses nestin, microtubule associated protein-5, neurofilament-200, vimentin and sodium-potassium ATPase; and
   said adult human retinal stem cells are introduced into the vitreous of said eye.

2. The method of claim 1 wherein said human is a neonate, a juvenile, or an adult.

3. The method of claim 1, wherein said stem cells integrate into and repopulate a diseased retina.

4. The method of claim 1, wherein said stem cells have survived in a culture medium for a period of about three months or greater.

5. The method of claim 1, wherein said stem cells comprise a cell line deposited with the American Type Culture Collection as Patent Deposit Designation No. PTA-7564.

6. The method of claim 1, wherein said human stem cells lack expression of glial fibrillary acidic protein (GFAP) or platelet/endothelial cell adhesion molecule-1 (PECAM).

* * * * *